United States Patent [19]

Rexroth et al.

[11] Patent Number: 4,943,290
[45] Date of Patent: Jul. 24, 1990

[54] ELECTROLYTE PURGING ELECTRODE TIP

[75] Inventors: Frederick W. Rexroth, Dunedin; F. Barry Bays, Seminole, both of Fla.

[73] Assignee: Concept Inc.

[21] Appl. No.: 343,730

[22] Filed: Apr. 27, 1989

Related U.S. Application Data

[63] Continuation of Ser. No. 65,823, Jun. 23, 1987.

[51] Int. Cl.⁵ ............................................. A61B 17/39
[52] U.S. Cl. ......................................... 606/45; 606/49
[58] Field of Search ..................... 128/303.13–303.18, 128/303.1; 606/45, 46, 48–50

[56] References Cited

U.S. PATENT DOCUMENTS

| | | | |
|---|---|---|---|
| 3,805,791 | 4/1974 | Seubarth | 128/303.14 |
| 3,900,022 | 8/1975 | Widran | 128/303.15 X |
| 4,068,667 | 1/1978 | Iglesias | 128/303.15 |
| 4,301,802 | 11/1981 | Poler | 128/303.14 |
| 4,325,374 | 4/1982 | Komiya | 128/303.15 |
| 4,449,528 | 5/1984 | Auth et al. | 128/303.1 |
| 4,532,924 | 8/1985 | Auth et al. | 128/303.17 |
| 4,562,838 | 1/1986 | Walker | 128/303.14 |
| 4,567,890 | 2/1986 | Ohta et al. | 128/303.13 |
| 4,593,691 | 6/1986 | Lindstrom et al. | 128/303.14 |
| 4,674,499 | 6/1987 | Pao | 128/303.14 |

FOREIGN PATENT DOCUMENTS

| | | | |
|---|---|---|---|
| 1007960 | 5/1957 | Fed. Rep. of Germany | 128/303.17 |
| 2930982 | 2/1981 | Fed. Rep. of Germany | 128/303.15 |
| 8605379 | 9/1986 | World Int. Prop. O. | 128/303.14 |
| 8605380 | 9/1986 | World Int. Prop. O. | 128/303.14 |

*Primary Examiner*—Lee S. Cohen
*Attorney, Agent, or Firm*—Frijouf, Rust & Pyle

[57] ABSTRACT

An electrolyte fluid purging electrosurgical device for use with an electrode holder connected to an electrical power source and to a source of a non-electrically conductive fluid and a method of use are disclosed. The fluid purging electrosurgical device enables electrosurgery at a surgical site where an area proximate the surgical site is surrounded by an electrically conductive fluid such as saline irrigation fluids, body fluids, certain injectables and the like. The fluid purging electrosurgical device comprises an electrode shaft with an electrode shaft connector electrically connecting a first end of the electrode shaft to an electrode holder. An insulating material provides electrical insulation between a second end of the electrode shaft and the electrode holder. The insulating material is positioned on the electrode shaft to expose a portion of the second end of the electrode shaft to define an electrode tip to provide electrical current to the surgical site. A duct means is connected to the source of the non-electrically conductive fluid and extends along the electrode shaft to deliver the non-electrically conductive fluid to a region immediately proximate the electrode tip to displace the electrically conductive fluid at the position of the electrode tip in the surgical site to enable electrosurgical treatment thereat.

7 Claims, 3 Drawing Sheets

ELECTROLYTE PURGING ELECTRODE TIP

This is a continuation of application Ser. No. 065,823 filed Jun. 23, 1987, the disclosure of which is incorporated herein by reference.

BACKGROUND OF THE INVENTION

1. Field of the Invention

This invention relates to electrosurgical appliances, and more specifically to a debris and electrolyte fluid purging electrosurgical device suitable for use with an arthroscopic system.

2. Information Disclosure Statement

The surgery accomplished by the use of electricity has progressed dramatically since the first introduction many years ago. Electrosurgery was first discovered to cause a "carbonization" or a cutting of a tissue when an electrosurgical electrode was located adjacent the tissue and to cause a "coagulation" of a tissue when the electrosurgical electrode was contacting a lesion or tissue. With the improvement of electrical generators, the discovery was made that a different type of electrical generator wave forms performed a different type of function on the lesions or tissues. A first or a moderately dampened wave form performs a strictly cutting function whereas a second or a substantially dampened wave form also performs a coagulation function. A third or a blended wave form combines the effect of cutting and coagulation although both the cutting and coagulation effects are somewhat diminished form the pure effects of coagulation and cutting.

Certain design changes have occurred for improving the electrical exposure of the electrode tip. These design changes were brought about by the understanding that electrical energy is dissipated from the electrode tip where the exposure of the electrode tip is large relative to the surgical site or where the exposure of the electrode tip is immersed in an operative site which is an electrically conductive environment because of electrically conductive fluids and the like. It was also learned that a larger exposed area of an electrode tip would require more power and be less efficient since there was a lower energy concentration. Furthermore, it was discovered that certain ionic solutions would also enhance the electrical dissipation from the electrode tip. For example, local anesthetics administered in a sodium chloride diluent infiltrated into the tissue and diminished the electrosurgical effects of the electrode tip. The presence of the sodium chloride enhanced the dissipation of the electrical energy. Accordingly, local anesthesia is not recommended in electrosurgical procedures. The electrical conductivity of blood will also interfere in the efficacy of the electrosurgical apparatus. The presence of the sodium chloride in the blood will cause dissipation of the electrical energy at the electrode tip. As a remedy to this problem, electrosurgical procedures require an irrigating solution with the irrigating solution is electrically non-conductive or non-ionic in nature. Therefore, during the surgical procedure, the presence of blood would necessitate the further irrigation of the operative site by an electrical non-conductive irrigation medium. A benefit of irrigating the site is that the involved area is distended allowing for better visibility of the injured area. Generally, sterile distilled water is used as the electrical non-conductive irrigation medium. However, other fluids such as air or carbon dioxide may sometimes be used in place of water. Air or carbon dioxide further provide distention of the knee joint during the surgical procedure to enable improved irrigation of the surgical site. However, the use of air or carbon dioxide is extremely dehydrating to the articular cartilage. Furthermore, carbon dioxide is extremely dehydrating and may unite with water present at the surgical site to form carbonic acid. Solutions of glycine or sorbitol are electrically non-conductive but are very viscous and can obscure the visual field of the surgical site.

Although the aforementioned prior art disclosures have aided in the development of electrosurgery, none of the aforementioned advances has satisfied the needs in the treatment and management of joint disorders in orthopedic practice. The use of arthroscopy in orthopedic practice has enabled orthopedic surgeons to directly visualize injury and disease sites and correct conditions with minimal incisions which only a few years ago would require an extensive open incision. However, the advent of arthroscopic surgery in the orthopedic practice has posed new problems to the manufacture of electrosurgical equipment. Among the most difficult problems in arthroscopic electrosurgery is the control of the conductive surgical environment of the surgical site within which the electrode tip must function. Present procedures utilize an electrically conductive isotonic solution, such as normal saline, to distend the surgical area in order to visualize the area. If electrosurgery is indicated, irrigation with an electrically conductive solution is terminated and irrigation with a non-electrically conductive solution is initiated.

It is a primary objective of this invention to provide an apparatus which overcomes the aforementioned difficulties of the prior art devices and provides an improvement which is a substantial contribution to the advancement of the electrical surgical electrode art.

Another object of this invention is to provide a fluid purging electrosurgical device which enables a surgeon to electrosurgically operate at an operative site which is contemporaneously irrigated by an electrically conductive solution such as normal saline or the like.

Another object of this invention is to provide a fluid purging electrosurgical device which is electrically operable in areas that are highly electrically resistant such as the meniscus cartilage and fat tissue.

Another object of this invention is to provide a fluid purging electrosurgical device which is applicable to many types of surgical operations but is specifically designed for arthroscopic surgery.

Another object of this invention is to provide a fluid purging electrosurgical device comprising an electrically conductive electrode tip which is electrically connected to a power source and which is in fluid communication with a fluid source to enable the electrode tip to be enveloped in a non-electrical conducting fluid thereby providing a non-electrical conductive and debris free operative site.

Another object of this invention is to provide a fluid purging electrosurgical device which is insulated and fluid tight.

Another object of this invention is to provide a fluid purging electrosurgical device wherein debris adjacent the operative site is forced from or purged from the operative site by the force of the purging electrically non-conductive fluid emanating from the duct means proximate the electrode tip.

Another object of this invention is to provide a fluid purging electrosurgical device with a fluid port which is integrally formed in the insulating means.

Another object of this invention is to provide a fluid purging electrosurgical device wherein the electrode tip and a region immediately proximate the electrode tip are enveloped in an electrically non-conductive fluid to enable electrosurgery with the enveloped electrode tip at a surgical site otherwise including the presence of electrically conductive fluids.

Another object of this invention is to provide a fluid purging electrosurgical device to prevent encroachment of an electrically conductive irrigation solution while minimizing any potential osmotic tissue damage to the irrigated operative site.

Another object of this invention is to provide a fluid purging electrosurgical device to prevent encroachment of debris and electrically conducting fluids proximate the electrosurgical site to enable the performance of the desired electrosurgical procedure.

Another object of this invention is to provide a fluid purging electrode which increases the efficiency of the electrosurgical operation by displacing of the normally present electrically conductive fluids and electrically conductive isotonic irrigation solution from the surgical site to enable concentration of the electrical energy of the electrode tip at the desired surgical site.

The foregoing has outlined some of the more pertinent objects of the present invention. These objects should be construed be to be merely illustrative of some of the more prominent features and applications of the invention. Many other beneficial results can be obtained by applying the disclosed invention in a different manner or modifying the invention within the scope of the invention. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

This invention is defined by the appended claims of the specific embodiment shown in the attached drawings. For the purpose of summarizing the invention, the invention may be incorporated into an apparatus comprising a fluid purging electrosurgical device for use with an electrode holder connected to an electrical power source and for use with a source of electrically non-conductive fluid for enabling electrical surgery at a surgical site where the surgical site is surrounded by an electrically conductive fluid. The fluid purging electrosurgical device comprises an electrically conductive electrode shaft having a first and a second end with an electrode shaft connecting means for electrically connecting the first end of the electrode shaft to the electrode holder. An insulating means extends along the electrode shaft for providing electrical insulation between the second end of the electrode and the electrode holder. The insulating means is positioned on the electrode shaft to expose a portion of the second end of the electrode shaft which defines an electrode tip to provide in use electrical current to the electrical site. A duct means is connected to a source of electrically non-conductive fluid for delivering the non-conductive fluid to a region proximate the electrode tip to displace the electrically conductive fluid and any debris present at the surgical site or generated during the surgical procedure from the surgical site thereby enabling electrical surgical treatment at that site.

In a further embodiment, the insulating means further includes an insulating coupler disposed proximate the first end of the electrode shaft for insulating the electrode shaft. More particularly, the insulating coupler includes an internal taper which cooperates with the electrode holder which has an external taper to provide electrical insulation and a seal which is waterproof between the first end of the electrode shaft and the electrode holder.

In one embodiment the duct means is disposed adjacent to and extends along the insulating means. In another embodiment, the duct means is integrally formed with the insulating means. In a further embodiment of the invention, the duct means comprises a plurality of channels disposed around the insulating means which electrically insulates the electrode shaft. Preferably, the number of channels which surround the electrode shaft is four. Most preferably, the number of channels which surround the electrode shaft is three. In another embodiment of the invention, an electrode shaft is centrally disposed within the plurality of channels. In a further embodiment of the electrosurgical device, the duct means is offset or not coaxially aligned with the electrode shaft.

In another embodiment of the invention, the duct means includes an input fluid port disposed proximate the first end of the electrode shaft for providing fluid communication with the source of non-conductive fluid. Optionally, the input fluid port provides a means for removably connecting the duct means to the source of non-conductive fluid.

In another embodiment, the electrode shaft connecting means includes a means for removably connecting the first end of the electrode shaft to the electrode holder. More specifically, the electrode shaft connecting means comprises a rounded or a chamfered first end of an electrode shaft which is received into an aperture of an insulting coupler, preferably made of an insulating plastic material.

The insulating means includes an insulating coupler disposed proximate the first end of the electrode shaft for insulating the electrode shaft connecting means. In a further embodiment of the invention, the insulating coupler further includes an internal taper and the electrode holder includes an external taper for cooperating with the internal taper of the insulating means to provide electrical insulation and a waterproof seal between the first end of the electrode shaft and the electrode holder.

In another embodiment of the invention, the electrode shaft is formed by providing an axial bore extended into the second end of the electrode rod for receiving the first end of a conductive electrode into the axial bore and securing the first end of the conductive electrode to the second end of the electrode rod. In the preferred that the second end of electrode rode is secured to the first end of the conductive electrode by a crimp(s). The incorporation of the crimp for securing the first end of the conductive electrode to the second end of the electrode rod enables the manufacturer to use electrodes having a different electrode tip with the same electrode rod and the same insulating coupling. The second end of the conductive electrode defines an electrode tip.

The input fluid port may further include a taper joint which cooperates with a delivery line from the source of non-conductive fluid to provide a removable fluid tight seal between the input port and delivery line from the source of non-conductive fluid. The taper joint further includes an external taper for frictionally engaging the inner diameter of the fluid delivery line of the source of the electrically non-conductive fluid to form a removable fluid tight seal.

In a specific embodiment of the invention, the electrolyte fluid purging electrosurgical device comprises an electrically conductive electrode shaft having a first and second end. An electrode shaft connecting means electrically connects in use the first end of the electrode shaft to the electrode holder. An insulating means extends along the electrode shaft for providing electrical insulation between the second end of the electrode shaft and the electrode holder. The insulating means is positioned on the electrode shaft to expose a portion of the second end of the electrode shaft to define an electrode tip for providing in use electrical current to the surgical site. A duct means includes a plurality of channels disposed within the insulating means for delivering in use the electrically non-conductive fluid to an area which is extremely proximate the electrode tip and includes the electrode tip itself, thereby displacing the electrically conductive fluid from the immediate area proximate the surgical site to enable electrosurgical treatment thereat. Preferably, the plurality of channels surround the electrode shaft.

In a further embodiment of the invention, the electrolyte fluid purging electrosurgical device comprises an electrically conductive electrode shaft having a first and a second end. An electrode shaft connecting means electrically connects in use the first end of the electrode shaft to the electrode holder. An insulating means extends along the electrode shaft for providing electrical insulation between the second end of the electrode shaft and the electrode holder. The insulating means is positioned on the electrode shaft to expose a portion of the second end of the electrode shaft to define an electrode tip which provides electrical current in use to the surgical site. The insulating means further includes an insulating coupler which includes an internal taper. The electrode holder includes an external taper which cooperates with the internal taper of the insulating coupler to provide in use electrical insulation and a waterproof seal when the electrode shaft connecting means is connected to the electrode holder. A duct means delivers the electrically non-conductive fluid proximate the surgical site. The duct means further include an input fluid port having a taper joint with an external taper for frictionally engaging an inner diameter of a delivery line in fluid communication with the source of the non-conductive fluid to form a removable fluid tight seal when the input fluid port and the source of the non-conductive fluid are connected together in use. The duct means further include a plurality of channels disposed within the insulating means for delivering the electrically non-conductive fluid to an area immediately proximate the electrode tip and about the electrode tip to displace the electrically conductive fluid from the area immediately proximate the surgical site to enable electrosurgical treatment thereat.

While any sterile non-electrical conducting fluid is within the scope of the invention, the preferred non-electrical conducting fluid is selected from the group consisting of sterile water, sterile distilled water (water for injection), carbon dioxide, glycine solution, sorbital solution and air. It is understood that sterile distilled water is a poor conductor of electricity since sterile distilled water is void of electrolytes. Accordingly, any form of non-electrolyte containing water will operate in the invention since non-electrolyte containing water is a poor conductor of electricity and thereby operable in the invention. Preferably, the concentrations of glycine and sorbital used are osmotically compatible with the tissue of the patient.

Preferably, the duct means and the insulating means are made of an electrically insulating plastic material.

The invention may also be incorporated into a method of performing electrosurgery at a surgical site bathed in an electrically conductive fluid described in greater detail below.

The foregoing has outlined rather broadly the more pertinent and important features of the present invention in order that the detailed description that follows may be better understood so that the present contribution to the art can be more fully appreciated. Additionally, features of the invention will be described hereinafter which form the subject of the claims of the invention. It should be appreciated by those skilled in the art that the conception and the specific embodiment disclosed may be readily utilized as a basis for modifying the preferred embodiment of the present invention by designing other devices for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention reference should be had to the following detailed description taken in conjunction with the accompanying drawings in which.

Similar reference characters refer to similar parts throughout the several views of the drawings.

DETAILED DESCRIPTION

Figure 1:
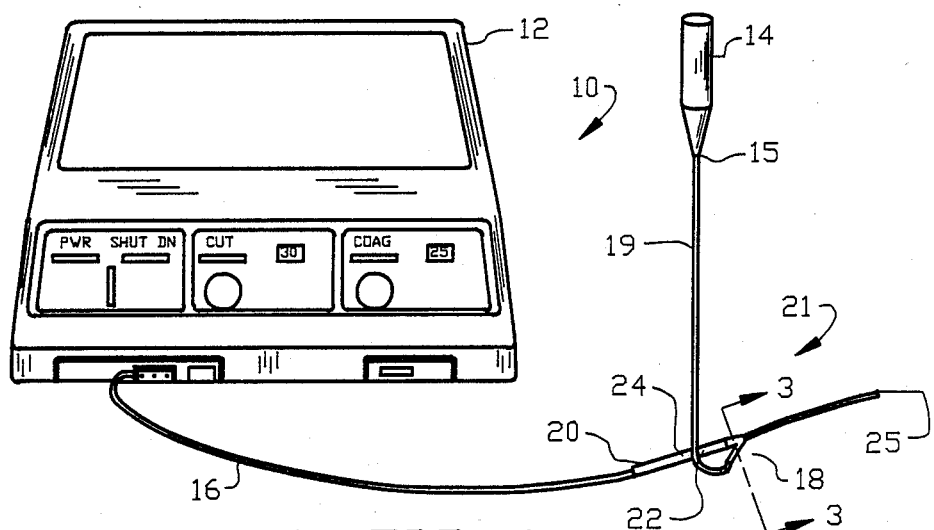
FIG. 1 is a perspective view of an electrosurgical apparatus incorporating the present invention.

FIG. 1 is an elevational view of a fluid purging electrosurgical apparatus 10 comprising an electronic control power source 12 shown as a radio frequency generator connected by an electrical line connector 16 to an electrode holder 20. An electrically non-conductive fluid source 14 is connected to an input fluid port 18 of a fluid purging electrode, referred to generally as 21, by an electrically non-conductive fluid delivery line 19. The flow rate of the electrically non-conductive fluid source 14 is controlled by a stopcock 15 which regulates the flow of the electrically non-conductive fluid through the fluid delivery line 19 to the surgical site during the electrosurgical operation at a pressure sufficient to displace the electrically conductive fluid proximate the electrode tip at the surgical site. In this embodiment, the electronic control power source 12 is a monopolar device with one polarity of electrical voltage being furnished through electrical connector 16 and with a second electrical connector (not shown) normally connected through a dispersive electrode connected to the patient as should be well known to those skilled in the art. Although a specific example has been shown for the electronic control power source 12, the electronic control power source, per se, does not form a part of the invention as will be apparent hereinafter.

The electrode holder 20 includes activating switches shown as push-button switches 22 and 24 for electrically connecting the electronic control power source 12 to a fluid purging electrode tip referred to generally as 25. The first switch 22 provides sufficient power to electrode tip 25 for cutting tissue whereas the second switch 24 provides limited power to electrode tip 25 for coagulation of tissue. Multiple switches 22 and 24 on the electrode holder 20 enable the cutting or the coagulating of tissue by a surgeon with the same electrode tip 25. During electrical operation of the electrosurgical apparatus 10, an electrically non-conductive fluid is dispensed from the non-conductive fluid source 14 to physically displace the electrically conductive fluids and the like in the region proximate the surgical site. The displacement of the electrically conductive fluids from the surgical site by the electrically non-conductive fluid enables the electrosurgical treatment to be undertaken with greater accuracy and at lower electrical power levels.

Figure 2:
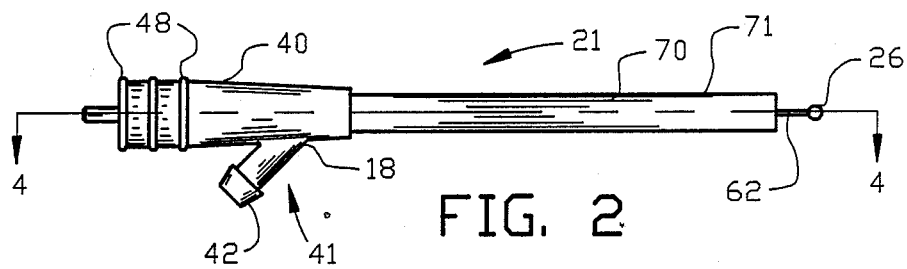
FIG. 2 is an elevational view of a first embodiment of a fluid purging electrode for use with the apparatus of FIG. 1.
Figure 3:
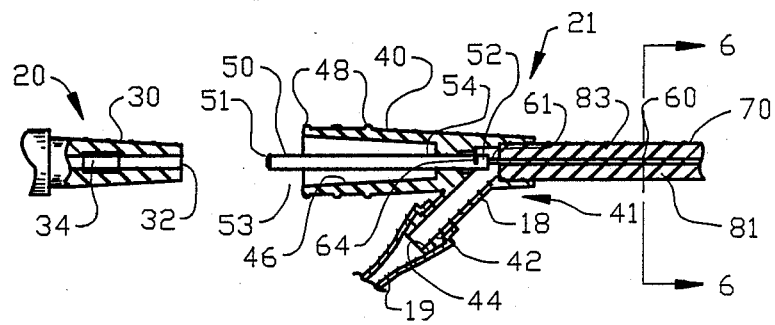
FIG. 3 is a partial sectional view along line 3—3 of FIG. 1.

FIG. 2 is an elevational view of the fluid purging electrode 21 of the l present invention with an electrode ball tip 26. FIG. 3 is an unassembled sectional view generally along the line 3—3 of FIG. 1 illustrating the electrode holder 20 having an external taper 30 and an axial aperture 32. The electrode holder 20 is preferably made of an insulating plastic material with a resilient metallic electrical connector 34 disposed within axial aperture 32 of the electrode holder 20 which metallic connector 34 is connected to switches 22 and 24 by conventional means not shown in FIG. 3.

FIG. 3 also illustrates an electrically insulating coupler 40 comprising an integrally formed fluid connector means 41 shown as a taper 42 for engaging an internal diameter 44 of the fluid delivery line 19 to connect the fluid source 14 to the input fluid port 18. The insulating coupler 40 includes an integrally formed electrode shaft connecting means 53 having an internal taper 46 for cooperation with the external taper 30 of the electrode holder 20 to provide a sealing relationship when the first end 51 of an electrode shaft 50 of the electrode shaft connecting means 53 is inserted within axial aperture 32 of the electrode holder 20 to electrically contact electrical connector 34. The first end 51 of the electrode shaft 50 is chamfered for facilitating the insertion of the first end 51 within the axial aperture 32 of the electrode holder 20. The electrode shaft 50 is preferably press fitted into a through aperture 54 in the insulating coupler 40. The insulating coupler 40 is preferably made of an insulating plastic material such as nylon to provide electrical insulation and to provide a fluid tight seal with the electrode holder 20. A friction engagement between the external taper 30 and the internal taper 46 provides a waterproof seal between the electrode holder 20 and the fluid purging electrode 21. Projections 48 disposed on an outer surface of the insulating coupling 40 facilitate the insertion and removal of the insulating coupling 40 on the electrode holder 20.

Figure 5:
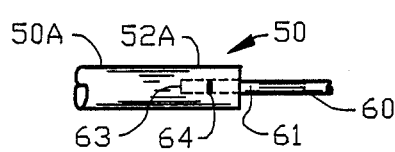
FIG. 5 is a partial view illustrating the crimping of an electrode rod to a conductive electrode.

FIG. 5 is a partial view illustrating the crimping of an electrode rod to a conductive electrode to form an electrode shaft 50. A first end 61 of a conductive electrode 60 is secured to a second end 52A of the electrode rod 50A with the second end 62 of the conductive electrode 60 defining an electrode tip 25. In the preferred form of the invention, the second end 52A of electrode rod 50A is secured to the first end 61 of conductive electrode 60 by a crimp 64. The incorporation of the crimp 64 for securing the first end 61 of the conductive electrode 60 to the second end 52A of the electrode rod 50A enables the manufacturer to use electrodes having a different electrode tip 25 with the same electrode rod 50A and the same insulating coupling 40.

Figure 4:
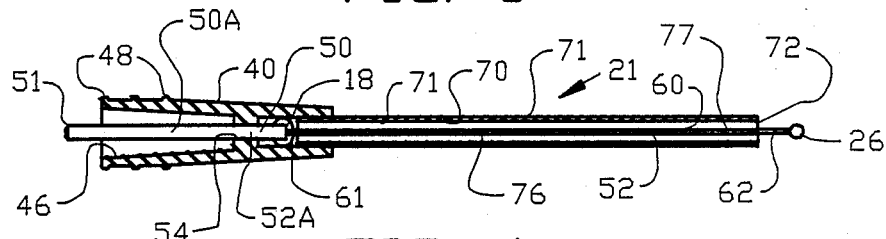
FIG. 4 is a partial sectional bottom view of the first embodiment of the fluid purging electrode taken along line 4—4 in FIG. 2.
Figure 6:
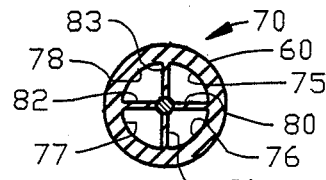
FIG. 6 is a sectional view along line 6—6 in FIG. 3 illustrating a duct means for the purging fluid.

FIGS. 4 and 6 illustrate the fluid purging electrode 21 including duct means 70 having a first end 71 and a second end 72 for directing in use the electrically non-conductive fluid from the fluid delivery source 14, the fluid delivery line 19 to the input fluid port 18 to the first end 71 of the duct means 70 and then to the second end 72 of the duct means. The non-conductive fluid then emanates from the second end 72 of the duct means 70 in use surrounds and envelopes the electrode tip 25. In another embodiment of the invention as shown in FIG. 6, the duct means 70 comprises a plurality of channels 75-78 with the conductive electrode 60 of the electrode shaft 50 being centrally located relative to the channels 75-78. A plurality of support walls 80-83 are integrally formed in the duct means 70 for supporting the conductive electrode 60 as well as providing a superior flow pattern of the non-conductive fluid at the second end 72 of the duct means 70 in proximity to the electrode tip 25. The duct means 70 is made of a suitable waterproof plastic material to provide electrical insulation for use in arthroscopic surgery. The insulating coupler 40 is bonded to the duct means 70 by a suitable bonding material such as a cyanoacrylate bonding material.

The fluid purging electrode 21 of FIGS. 2-9 may be constructed, for example, by first inserting the first end 61 of the conductive electrode 60 into the second end 72 of the duct means 70 formed within the insulating means 71 in a manner such that a portion of the second end of the electrode shaft 50 is exposed to define an electrode tip 25. The first end 61 of the conductive electrode 60 is then inserted into an axial bore 63 axially formed within the second end 52A of the electrode rod 50A and is secured therein by a crimp(s) 64. A bonding material is then applied to either or both the insulating coupling 40 and the duct means 70. An aperture 43A of insulating coupling 40 slidably receives the first end 51A of the electrode 50A forming a seal 43 between the insulating coupling 40 and the duct means 70.

Figure 14:
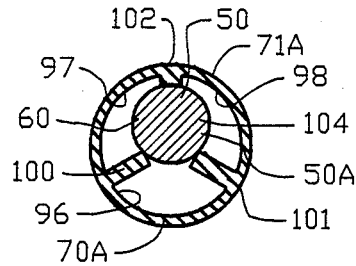
FIG. 14 is a sectional view along line 14—14 in FIG. 13 illustrating an offset electrode rod positioned in the duct means for the purging fluid.
Figure 15:
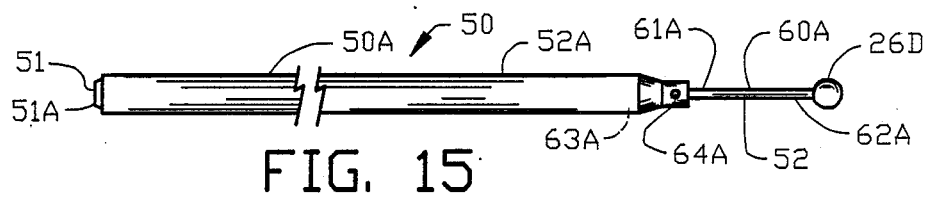
FIG. 15 is an elevational view illustrating the preferred embodiment of an electrode shaft and electrode with the crimping of an electrode rod to the conductive electrode.

The preferred embodiment of the fluid purged electrode (FIGS. 13-18) may be constructed by first inserting the first end 61A of a conductive electrode 60A into an axial bore 63A axially formed within the second end 52A of electrode rod 50A and secured by crimp(s) 64A as illustrated at FIG. 15. Then the first end 51A of electrode rod 50A is inserted into second end 72A of duct means 70A formed within the insulating means 71A until second end 62A of conductive electrode 60A is exposed a length sufficient to enable electrosurgery. The first end 51A of electrode rod 50A is then oriented relative the orientation bump 94 and placed in an insert mold apparatus to allow the insulating coupler 40A to be insert molded about the first end 74A of duct means 70A. As is evident from FIG. 15, the relative length of the electrode rod 50A is greater than the length of conductive electrode 60A. Whereas, the relative length of conductive rod 60 is greater than the length of electrode rod 50A as illustrated at FIGS. 4-9. Each of the above methods of construction forms an electrically conductive electrode shaft 50.

The operation of the electrosurgical apparatus 10 should be apparent from the description of the apparatus. The fluid purging electrode 21 is inserted on the electrode holder 20 with the external taper 30 engaging the internal taper 46 to form a waterproof seal between the fluid purging electrode 21 and the electrode holder 20. Preferably, the electrode 21 is removable from the electrode holder 20 to enable the use of different electrode tips 25 associated with different fluid purging electrodes 21. The fluid delivery line 19 is then secured to the input fluid port 18. The fluid purging electrode 21 may then be inserted into an incision in a patient prepared for electrosurgery. The stopcock 15 is adjusted to provide the proper fluid flow rate of the electrically non-conductive fluid to displace the electrically conductive body fluids from the surgical site proximate the electrode tip 25. Other means for providing pressurization of the electrically non-conductive fluid, such as a pump, may be substituted for the gravity supplied non-conductive fluid as illustrated in FIG. 1. The surgeon may the utilize switches 22 and 24 to complete the electrosurgical procedure proximate the electrode tip 25 at the surgical site.

FIGS. 2 and 4 illustrate the electrode tip 25 as an electrode ball tip 26 which is integrally formed on the second end 62 of the conductive electrode 60 with the first end 61 of the conductive electrode 60 being received into an axial bore 63 formed in the second end 52A of the electrode rod 50A and secured therein by a crimp 64 to form an electrode shaft 50.

Figure 7:
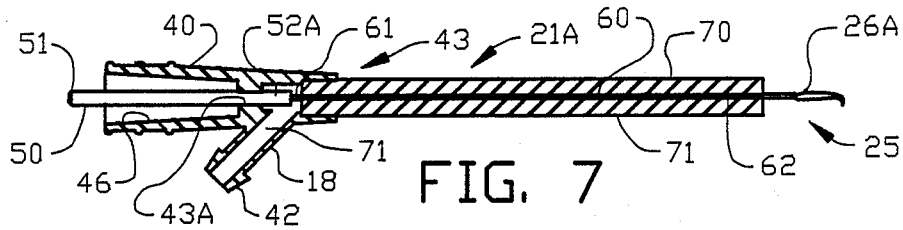
FIG. 7 is a partial sectional view of a second embodiment of the fluid purging electrode incorporating a soft tissue electrode tip.

FIG. 7 is a partial sectional view of a fluid purging electrode 21A similar to the fluid purging electrode 21 shown in FIGS. 2-6. In this embodiment, the electrode tip 25 is shown as a soft tissue electrode tip 26A. A method of forming an electrode shaft 50 with a soft tissue electrode tip 26A is as described hereinbefore, but with the use of tip 26A.

Figure 8:
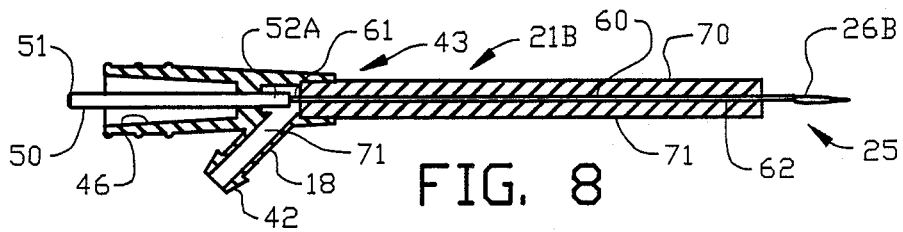
FIG. 8 is a partial sectional view of a third embodiment of the fluid purging electrode incorporating a dagger electrode tip.

FIG. 8 is a partial sectional view of a fluid purging electrode 21B similar to the fluid purging electrode 21 shown in FIGS. 2-6. In this embodiment, the electrode tip 25 is shown as a dagger tip electrode 26B. A method of forming an electrode shaft 50 with a dagger tip electrode 26B is as described hereinbefore, but with the use of tip 26B.

Figure 9:
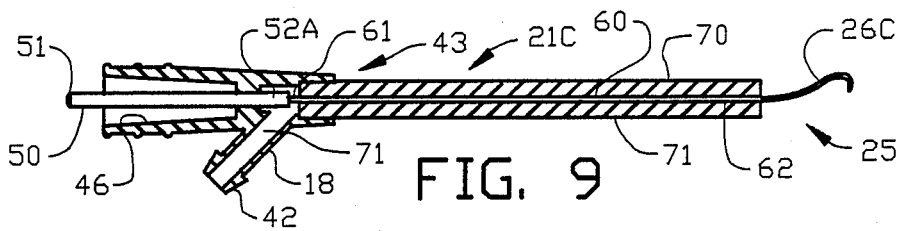
FIG. 9 is a partial sectional view of a fourth embodiment of the fluid purging electrode incorporating a meniscectomy electrode tip.

FIG. 9 is a partial sectional view of a fluid purging electrode 21C similar to the fluid purging electrode 21 shown in FIGS. 2-6. In this embodiment, fluid purging electrode 21C incorporates a meniscectomy electrode tip 26C which is formed as described above. FIGS. 2-9 illustrate that various types of electrode tips may be incorporated into the present invention without modification of the remaining components of the fluid purging electrode.

The electrode tips 26A, 26B and 26C shown in FIGS. 7, 8 and 9 respectively are non-symmetrical about an axis extending through the conductive electrode 60. The major dimension of the electrode tips 26A, 26B and 26C extends in a plane which plane is contained in the plane of the drawings. The input fluid port 18 is similarly disposed in the plane of the drawings for assisting the surgeon in orientating the major dimension of the electrode tips 26A, 26B and 26C through the orientation of the input fluid port 18 when the electrode tips 26A, 26B and 26C are located within an incision.

Figure 10:
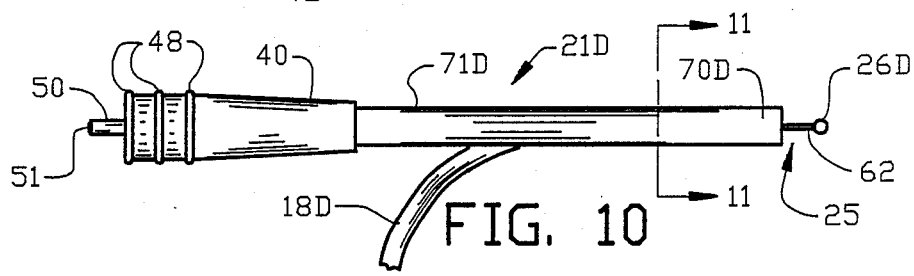
FIG. 10 is a elevational view of another embodiment of the fluid purging electrode for use with the apparatus of FIG. 1.
Figure 11:
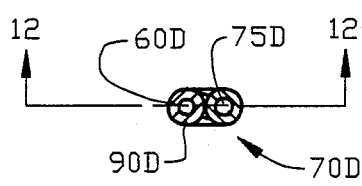
FIG. 11 is a sectional view taken along the line 11—11 of FIG. 10.
Figure 12:
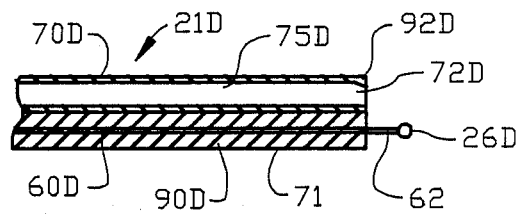
FIG. 12 is a sectional veiw taken along the line 12—12 of FIG. 11.

FIGS. 10-12 illustrate various views of a further embodiment of the fluid purging electrode 21D for use with the apparatus of FIG. 1. In this embodiment, the duct means 70D is provided by an electrically insulating tubing in fluid communication with the fluid source 14 through a input fluid port 18D. The duct means 70D comprises a single channel 75D which is integrally formed along with insulating means shown as an insulating tubing 90D. The insulating tubing 90D receives a conductive electrode 60D therein as shown in greater detail in FIG. 12. The second end 72D of duct 70D includes a deflector 92D to direct the fluid emanating from the second end 72D of duct means 70D to envelop the electrode tip 26D in order to displace electrically conductive fluids from the surgical site proximate the electrode tip 26D during electrosurgery. In this embodiment, the duct means 70D is integrally formed and disposed adjacent to the insulating tubing 90D as illustrated at FIG. 11. Other electrode tips such as 26A, 26B and 26C, may be used in place of tip 26D as shown in FIGS. 10 and 12.

Figure 13:
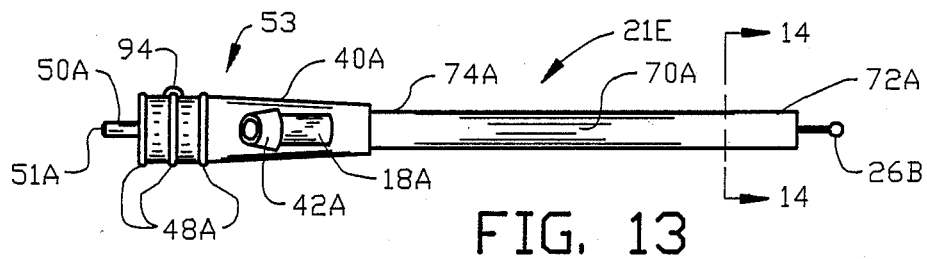
FIG. 13 is a top view of the preferred embodiment of a fluid purging electrode incorporating a dagger electrode tip for use with the apparatus of FIG. 1.

FIG. 13 is a top view of the preferred embodiment of the fluid purging electrode 21E of the present invention for use with the apparatus of FIG. 1. The insulating coupler 40A includes an integrally formed electrode connector means 53. In this embodiment, the duct means 70A is provided by an electrically insulating tubing in fluid communication with the fluid source 14 through an input fluid port 18A. Preferably, the duct means which provides a conduit for the electrically non-conductive fluid is formed within an electrically insulating plastic material. The duct means 70A comprises three support walls 100–102, as shown in FIG. 14, integrally formed therein for supporting electrode rod 50A as well as providing a superior flow pattern of the non-conductive fluid to displace electrically conductive fluids and debris from the surgical site proximate the electrode tip 26B at the second end 72A of duct means 70A. More specifically, the three support walls 100–102 establish channels 96, 97 and 98 with the electrode rod 50A is positioned in an offset manner relative the geometric center 104 of duct means 70A. As shown in FIG. 14, supporting walls 100 and 101 are of a greater length relative supporting wall 101 thereby enabling channels 97 and 98 to have a smaller cross-sectional area relative channels 97 and 98 to have a smaller cross-sectional area relative channel 96. As shown in FIG. 13 projections 48A disposed on an outer surface of the insulating coupling 40A facilitate the insertion and removal of the insulating coupling 40A on the electrode holder 20. The major dimension of the electrode tips 26A, 26B and 26C extends in a plane which plane is contained in the plane of the drawings. Orientation bump 94 on the surface of insulating coupling 40A is similarly disposed in the plane of the drawings for assisting the surgeon in orientating the major dimension of electrode tips 26A, 26B and 26C through orientation of bump 94 when the electrode tips 26A, 26B and 26C are located within an incision. The plane of the blade tip is in-line with the orientation bump within ±10 degrees. This orientation applies to any electrode tip 25 with a blade or a non-symmetrical tip where orientation of the tip is helpful to a surgeon.

Figure 16:
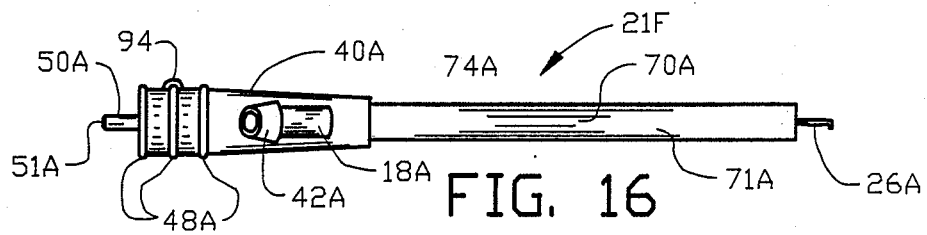
FIG. 16 is a top view of a preferred embodiment of the fluid purging electrode incorporating a soft tissue electrode tip.

FIG. 16 is a top view of a preferred embodiment of the fluid purging electrode 21F incorporating a soft tissue electrode tip 26A.

Figure 17:
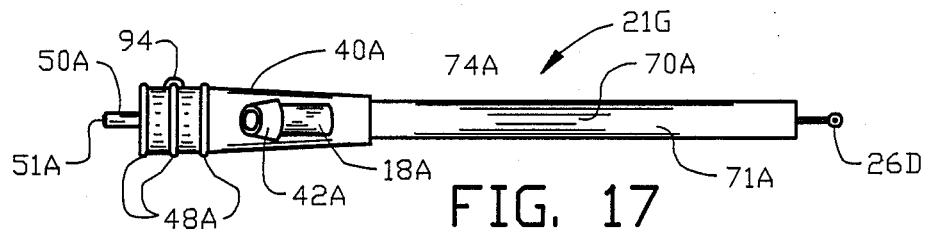
FIG. 17 is a top view of another preferred embodiment of the fluid purging electrode incorporating an electrode ball tip.

FIG. 17 is a top view of another preferred embodiment of the fluid purging electrode 21G incorporating an electrode ball tip 26D.

Figure 18:
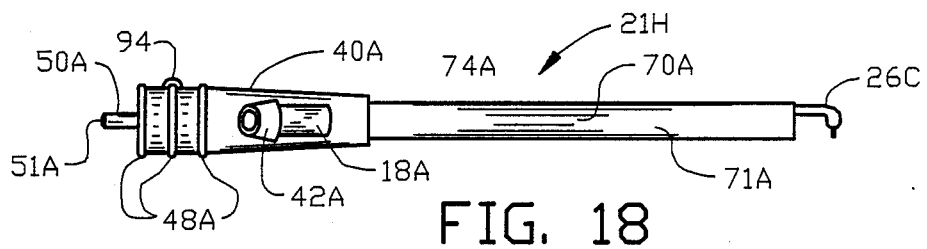
FIG. 18 is a top view of a preferred embodiment of the fluid purging electrode incorporating a meniscectomy electrode tip.

FIG. 18 is a top view of a preferred embodiment of the fluid purging electrode 21H incorporating a meniscectomy electrode tip 26C.

The electrode shaft connecting means 53 includes the structure necessary for electrically connecting the first end 51 of the electrode shaft 50 to the electrode holder 20. More specifically, the electrode shaft connecting means provides a structure which insures that the first end 51 of the electrode shaft 50 is electrically connected to electrical connector 34 of the electrode holder 20. For example, an alternative electrode shaft connecting means embraced by the invention is described by using an electrical line connector 16 from power source 12 integrally formed with electrode 21 and electrically connected to the electrode shaft 50 such that the holder 20 and the electrode 21 are formed as a single unit which do not separate. The removable electrode shaft connecting means is illustrated in, for example, FIG. 2.

A further embodiment of the invention includes a method of performing electrosurgery at a surgical site which is suitable for electrosurgery as known by one skilled in the art and which is surrounded by an electrically conductive fluid, including physiological fluids, such as blood, electrically conductive irrigation fluid, electrically conductive injectable, and the like. The method comprises the steps of providing an electrosurgical apparatus for performing electrosurgery and preparing the patient and the intended surgical site for electrosurgery surgery. The electrosurgical apparatus is prepared for electrosurgery at the surgical site on the patient. A flow of electrically conductive physiological fluid is initiated and maintained, such as physiological salt solution, for irrigating an area greater than, and inclulding, the area of the intended electrosurgical site. An electrically non-conductive fluid is delivered under pressure proximate the surgical site to purge only the immediate proximate surgical site consisting of the immediate area or a portion thereof of the intended electrosurgical site, of any electrically conductive fluid. Contact of the purged surgical site with an activated electrosurgical electrode is initiated, preferably simultaneously, with the electrically non-conductive fluid flow to enable the performance of the desired electrosurgical procedure at the purged surgical site without interference by the electrically conductive fluid flow which is maintained while performing the desired electrosurgical procedure.

An improved method of performing an arthroscopic subcutaneous lateral release with an electrosurgical cautery on a patient in need of such arthroscopic subcutaneous lateral release and where the surgical site is surrounded by an electrically conductive fluid is disclosed. The method comprises the steps of providing an electrosurgical apparatus for performing electrosurgery. The patient and the intended surgical site is then prepared for arthroscopic surgery. The electrosurgical apparatus is prepared for electrosurgery at the surgical site on the patient. An electrically conductive physiological salt solution is established to irrigate an area greater than, and including, the area of the intended subcutaneous lateral release site. Prior to performing electrosurgery at the intended site, the electrically conductive physiological salt solution is stopped and an electrically non-conductive sterile water is initiated to irrigate the area greater than and including the area of the intended subcutaneous lateral release site to enable the performance of electrosurgery without interference from the electrically conductive fluid. Arthroscopic electrosurgery is now performed at the intended surgical site. The improvement of the above method comrises the steps of initiating and maintaining an electrically conductive physiological irrigation fluid in an area greater than, and including, the area of the intended subcutaneous lateral release site. An electrically non-conductive fluid under pressure is delivered proximate the surgical site to purge only the immediate proximate surgical site consisting of the immediate area or a portion thereof of the intended subcutaneous lateral release site, of any electrically conductive fluid. Contact of the purged surgical site with an activated electrosurgical electrode is initiated, preferably simultaneously, with the electrically non-conductive fluid flow to enable the performance of the desired electrosurgical procedure at the purged surgical site without interference by the electrically conductive fluid flow being maintained while performing the desired electrosurgical procedure of the subcutaneous lateral release.

More specifically, the improved method of performing an arthroscopic subcutaneous lateral release utilizing an electrosurgical cautery on a patient in need of an arthroscopic subcutaneous lateral release where the surgical site is surrounded by an electrically conductive fluid comprising the steps of administering an adequate anesthesia to the patient and applying an uninflated tourniquet to the upper thigh of the patient. An electrical grounding pad is applied to the patient and the involved area is readied for surgery by disinfecting the area. A saline inflow cannula is established in the suprapatellar pouch. An anterolateral portal is established and an arthroscope is introduced therein to enable examination with a television video system. The electrically conductive saline irrigation is converted to electrically non-conductive sterile water. A needle is inserted along the lateral margin of the quadriceps tendon just proximal to the superior pole of the patella which acts as a visible marker for the proximal extent of the release. An anteromedial portal is established and the anthroscope is removed from the anterolateral portal and inserted into the anteromedial portal to visualize the spinal needle. An electrosurgical cautery is inserted into the anterolateral portal and the tip of the cautery is positioned at the site of the spinal needle. The cutting mode of the electrosurgical cautery is used to divide the lateral patellofemoral ligament and retinaculum progressing distally about 1 centimeter from the lateral patellar margin. The cauterizing mode of the electrosurgical cautery is utilized to sequentially cauterize all vessels as transected where the tourniquet is not inflated. However, where the tourniquet was inflated, cauterize all bleeding vessels to control bleeding when deinflated. Insure that the patella has been centralized and apply adequate dressing to the involved area. The improvement of the above method comprises maintaining the electrically conductive saline irrigation in the superpatellar pouch and inserting an electrosurgical cautery with an electrolyte fluid purging electrode tip in the anterolateral portal and positioning the tip of the cautery at the site of the spinal needle. A flow of an electrically non-conductive fluid is initiated and continued immediately proximate the activated cautery tip sufficient to displace the electrically conductive fluid and any other debris proximate the cautery tip to enable electrosurgery at the surgical site during the flow of electrically non-conductive fluid. In a further embodiment, the flow of the electrically non-conductive fluid is initiated only when the cautery tip is electrically activated. The cutting mode is utilized to divide the lateral patellofemoral ligament and retinaculum progressing distally about 1 centimeter from the lateral patellar margin.

The preferred electrically non-conductive fluid in the method of performing an arthroscopic subcutaneous lateral release is sterile distilled water.

The present invention includes that contained in the appended claims as well as that of the foregoing description. Although this invention has been described in its preferred form with a certain degree of particularly, it is understood that the present disclosure of the preferred form has been made only by way of example and that numerous changes in the details of construction and the combination and arrangement of parts may be resorted to without departing from the spirit and scope of the invention.

What is claimed is:

1. An electrolyte fluid purging electrosurgical device for use with an electrode holder connected to an electrical power source and with a source of non-electrically conductive fluid for enabling electrosurgery at a surgical site which is surrounded by an electrically conductive fluid, comprising:

an electrically conductive electrode shaft having a first electrode end and a second electrode end;

an insulating tubular duct defining a duct conduit extending between a first duct end and a second duct end;

said electrode shaft being disposed within said duct conduit with said first electrode end of said electrode shaft extending beyond said first duct end of said insulating tubular duct for defining an electrode shaft connecting means for connection to the electrode holder;

said second electrode end of said electrode shaft extending beyond said second duct end of said insulating tubular duct for defining an electrode tip to provide electrical current to the surgical site;

a plurality of support walls extending longitudinally within said duct conduit of said insulating tubular duct and disposed between said insulating tubular duct and said electrode shaft for supporting said electrode shaft within said duct conduit of said insulating tubular duct and for defining a plurality of conduit channels encompassing said electrode shaft; and means for connecting said first duct end of said insulating tubular duct to the source of non-electrically conductive fluid for enabling non-electrically conductive fluid to flow through said plurality of conduit channels of said insulating tubular duct to deliver the electrically non-conductive fluid to an immediate area proximate said electrode tip to displace the electrically conductive fluid from the immediate area proximate the surgical site when said electrode tip is positioned at the surgical site to enable electrosurgical treatment thereat.

2. The electrolyte fluid purging electrosurgical device of claim 1, wherein said electrode shaft connecting means includes means for removably connecting said electrode shaft to the electrode holder.

3. The electrolyte fluid purging electrosurgical device of claim 1, wherein said electrode shaft is coaxially aligned within said duct conduit of said insulating tubular duct; and said plurality of conduit channels uniformly surrounding said electrode shaft.

4. The electrolyte fluid purging electrosurgical device of claim 1, wherein said plurality of support walls are integrally formed with said insulating tubular duct.

5. The electrolyte fluid purging electrosurgical device of claim 1, wherein said means for connecting said first duct end includes an input fluid port disposed proximate said first duct end for removably connecting said insulating tubular duct to the source of the electrically non-conductive fluid.

6. The electrolyte fluid purging electrosurgical electrode of claim 5, wherein said input fluid port further includes a taper joint which includes an external taper for frictionally engaging an inner diameter of a fluid delivery line in fluid communication with the source of the non-conductive fluid to form a removable fluid tight seal between said fluid delivery line and said input fluid port.

7. The electrolyte fluid purging electrosurgical device of claim 1, including an insulating coupler disposed proximate said first duct end of said insulating tubular duct; and said insulating coupler including an internal taper for cooperating with an external taper of the electrode holder to provide electrical insulation and a waterproof seal when said electrode shaft connecting means is connected to the electrode holder.

* * * * *